(12) United States Patent
Suzuki (10) Patent No.: US 7,357,508 B2
(45) Date of Patent: Apr. 15, 2008

(54) EYE TEST CHART APPARATUS (76) Inventor: Taketoshi Suzuki, 16, Kichikouji, Mizusawa-shi, Iwate-ken 023-0054 (JP)

( * ) Notice: Subject to any disclaimer, the term of this patent is extended or adjusted under 35 U.S.C. 154(b) by 692 days.

(21) Appl. No.: 10/487,784

(22) PCT Filed: Aug. 23, 2002

(86) PCT No.: PCT/JP02/08510

§ 371 (c)(1),
(2), (4) Date: Feb. 26, 2004

(87) PCT Pub. No.: WO03/017830

PCT Pub. Date: Mar. 6, 2003

(65) Prior Publication Data

US 2004/0207813 A1    Oct. 21, 2004

(30) Foreign Application Priority Data

Aug. 27, 2001 (JP) ............................. 2001-256534
Jul. 19, 2002 (JP) ............................. 2002-211514

(51) Int. Cl.
*A61B 3/02* (2006.01)
(52) U.S. Cl. .................................................. 351/239
(58) Field of Classification Search ................ 351/237, 351/238, 239, 240, 242, 243; 345/22, 23, 345/25, 156
See application file for complete search history.

(56) References Cited

U.S. PATENT DOCUMENTS 5,844,544 A * 12/1998 Kahn et al. ................. 345/156

6,379,007 B1 * 4/2002 Farb ........................... 351/239

FOREIGN PATENT DOCUMENTS

| JP | 61-0144516 A1 | 7/1986 |
| JP | 04-014972 B2 | 6/1989 |
| JP | 01-036483 Y2 | 11/1989 |
| JP | 02-029325 B2 | 6/1990 |
| JP | 04-012730 A1 | 1/1992 |
| JP | 05-168593 A1 | 7/1993 |
| JP | 05-088501 U1 | 12/1993 |
| JP | 06-237895 A1 | 8/1994 |
| JP | 11-009550 A1 | 1/1999 |
| JP | 11-032991 A1 | 2/1999 |

OTHER PUBLICATIONS

International Search Report for PCT/JP02/08510 mailed on Nov. 26, 2002.

* cited by examiner

*Primary Examiner*—M. Hasan
(74) *Attorney, Agent, or Firm*—Rader, Fishman & Grauer PLLC

(57) ABSTRACT

An eye test chart includes a visual target for multiple test purposes composed of patterns of combinations of at lest two or more kinds of colors and predetermined shapes that are arranged at predetermined positions on an image area corresponding to visual field regions to be examined. Color vision defects and their abnormal regions can be identified as a result of a subject's visual identification of the visual targets arranged at the predetermined positions.

16 Claims, 7 Drawing Sheets

EYE TEST CHART APPARATUS

TECHNICAL FIELD

The present invention relates to an eye test chart used for examining visual field defects, metamorphopsia, or color defective vision caused by eye diseases, such as those of the retina and optic nerve, or intracranial diseases etc., and particularly to an eye test chart capable of making easy the detection of early symptoms or progress observation.

BACKGROUND ART

Tests on vision are important not only in ophthalmology to diagnose eye diseases such as those of the retina and optic nerve, but also in neurology or brain surgery to diagnose intracranial diseases, and various kinds of test apparatuses or charts, such as Goldmann perimeter and Humphrey perimeter, have been conventionally used.

Test methods using conventional apparatuses or charts, however, limit test items to one per apparatus or chart. When multiple test items such as metamorphopsia and color defective vision need testing, multiple apparatuses or charts are needed for the test, which is time-consuming and troublesome. In addition to being troublesome, it requires the continuous attention of persons being tested, or subjects, causing their fatigue. Furthermore, the use of the conventional test apparatuses or charts makes it difficult for the subjects to become aware of their abnormal regions, and hence to figure out their symptoms.

Further, since conventional test apparatuses are very big, floor-mounted type apparatuses, they are difficult to carry around. In the case of the use of a test apparatus using light as a visual target, a test-specific space and environment that provide a "semidark" room has been required. In such a case, any subject has to come over to the installation site of the test apparatus and maintain a predetermined position to undergo a test, and this makes it very difficult for bedridden patients to undergo the test.

Further, a patient who is not aware of early symptoms of each disease causing visual impairment does not know that he or she has the disease until after the disease reaches such an advanced stage that subjective symptoms appear, he or she visits a medical institution and the disease is diagnosed by ophthalmology. Thus there has been a problem that early detection of the disease is difficult.

Therefore, the development of an eye test chart capable of carrying out eye tests of multiple items simultaneously and easily has been strongly desired.

DISCLOSURE OF THE INVENTION

It is an object of the present invention to provide an innovative eye test chart that meets such a desire.

According the present invention, there is provided an eye test chart on which multiple visual targets composed of patterns of combinations of at least two or more kinds of colors are arranged at predetermined positions corresponding to visual field regions to be examined. Using this chart, it is checked whether the combinations of colors and the shapes different in the position of the targets can be identified or not, thus carrying out detailed eye tests for each region to be examined.

In one preferred embodiment, the visual targets include circular or square targets of two or more kinds of colors different in hue and complementary to each other. Based on such a figuration, it is checked whether the shapes or profile straight or curved lines can be visually correctly identified, thereby enabling the detection of visual impairment. Since the colors are different in hue, it is easy to visually identify the visual targets, and if they are complementary colors, it will be further easier to visually identify them. Then, it is checked whether the colored conditions can be visually correctly identified, thereby also enabling the examination of the presence or absence of color defective vision. The visual targets also include circular or square targets divided into four parts in a checkered pattern of a combination of two kinds of colors different from the background color, or circular or square targets each composed of a vertical striped pattern of two kinds of colors. It is checked whether they can be visually correctly identified to enable the examination of the presence or absence of visual field defects and metamorphopsia. The direction of the striped pattern may be changed to determine the astigmatic direction. In addition, the striped pattern is formed such that one color shifts to the other in a sinusoidal fashion. This makes it easy to detect a pathological blind spot in the macular area, that is, even in a part where sensitivity is reduced. On the eye test chart, a fixed target having a color or colors different from those of said circular or square targets, or a profile line (grid, etc.) bolder than those of the other targets is also arranged at the center. Then, grid targets composed of a grid of squares in which the circular or square targets are displayed are arranged in parallel around the fixed target in both the longitudinal and transverse directions. Using this chart, it is checked whether there are parts in the chart that look missing or disappear from the eye, whether the grid squares of the grid targets look skewed, and whether the striped pattern or checkered pattern can be visually correctly identified. It allows the examination of the presence or absence of central and paracentral visual field defects and metamorphopsia. Further, enlarged circular or square targets formed by just enlarging the pattern of the circular or square targets arranged inside the grid targets are arranged vertically and horizontally in parallel to enable the detection of a visual field detect even in a person with low visual acuity.

In another preferred embodiment, band-shaped targets formed in the shape of a band with a checkered pattern of multiple squares, each composed of the striped pattern or checkered pattern with the four divided parts, are arranged around the central portion of the eye test chart vertically and horizontally in parallel. It allows the detection of a visual field defect in the Bjerrum area. The difference in color, rather than the striped pattern, is used to identify the four-divided squares in the checkered pattern so that the band-shaped targets can be identified even by the eye with low sensitivity. On the eye test chart, a set of blind-point targets for determining Mariotte's blind spot, composed of a combination of one or more black figures, is also arranged at a predetermined bilateral position, so that the proper positional relation between the chart and the eye can be maintained, thereby carrying out the eye tests easily and accurately. Further, multiple blind-spot peripheral targets colored with a color different from the background color and easy to visually identify are arranged around the blind-spot targets in a bilaterally symmetrical pattern. The use of the blind-spot peripheral targets makes it possible to check whether the extent of Mariotte's blind spot is widened. In addition, large-sized square targets, each of which is a black square larger than any other single circular or square target, and which contains two figures colored with the background color or a color of high lightness and spaced at a predetermined interval, are arranged on four corners of the eye test chart. Then, at least two or more parallel square targets, each of which is composed of a hollow figure shaped like a Chinese character "日" with the figure parts colored with a color different from the background color and easy to visually identify and the hollow parts colored with the background color, are arranged at both top and bottom sides, or at both right and left sides, in parallel in the transverse or longitudinal direction. Further, at least two or more parallel circular targets, each of which is composed of a hollow figure shaped like a number "0" with the figure parts colored with a color different from the background color and easy to visually identify and the hollow parts colored with the background color, are arranged at both top and bottom sides, or at both right and left sides, in parallel in the transverse or longitudinal direction. The use of these targets different in shape and color enables the examination of the eye's resolution in each disease region and each stage of the disease. These targets can also be used to a detect visual field detect or hemianopia, and further a nasal step in glaucoma.

All the above-mentioned targets are arranged in a bilaterally symmetrical pattern to enable an accurate comparison of visual impairment in both right and left eyes.

BEST MODES FOR CARRYING OUT THE INVENTION

The present invention will now be described in more detail according to the accompanying drawings.

Figure 1:
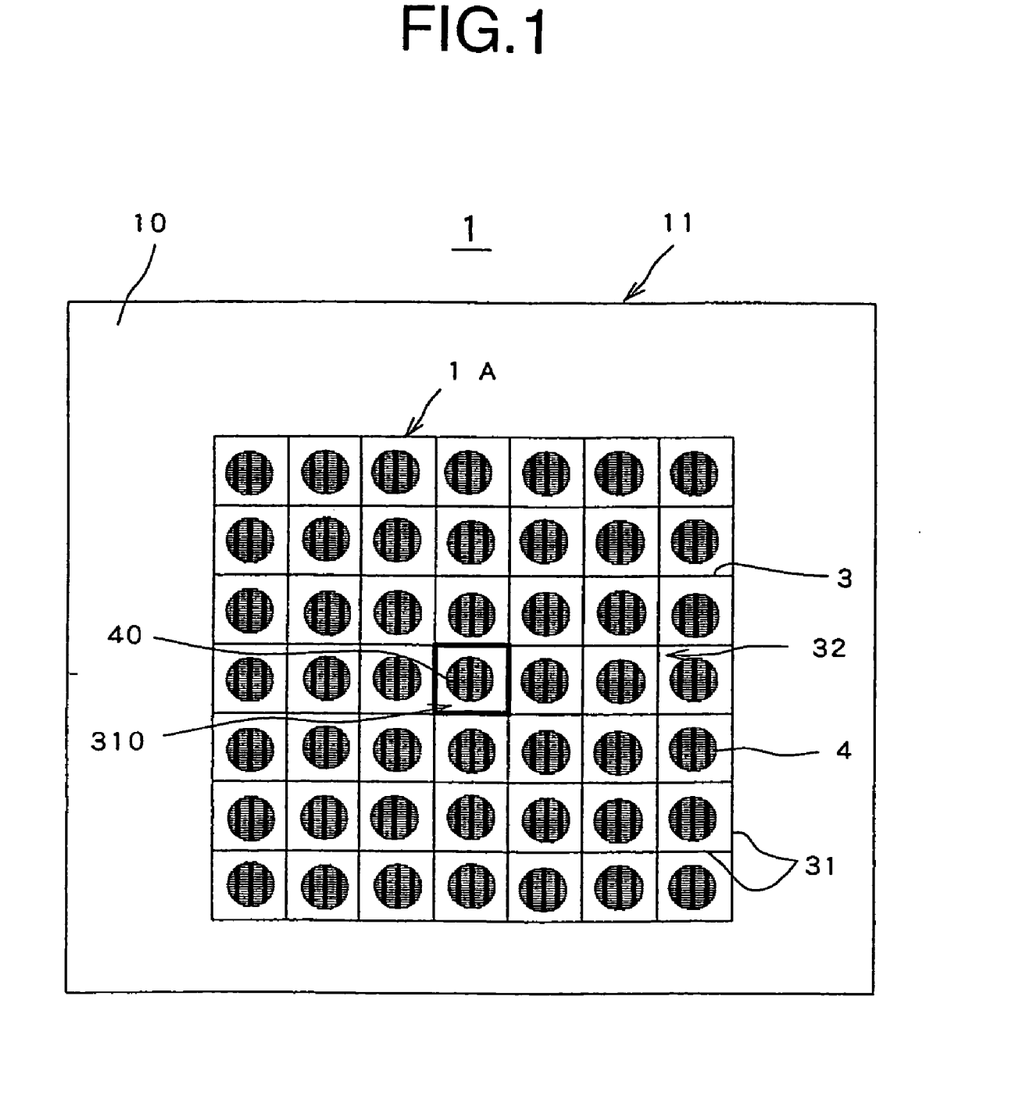
FIG. 1 is a front view showing a preferred eye test chart according to the present invention.
Figure 2:
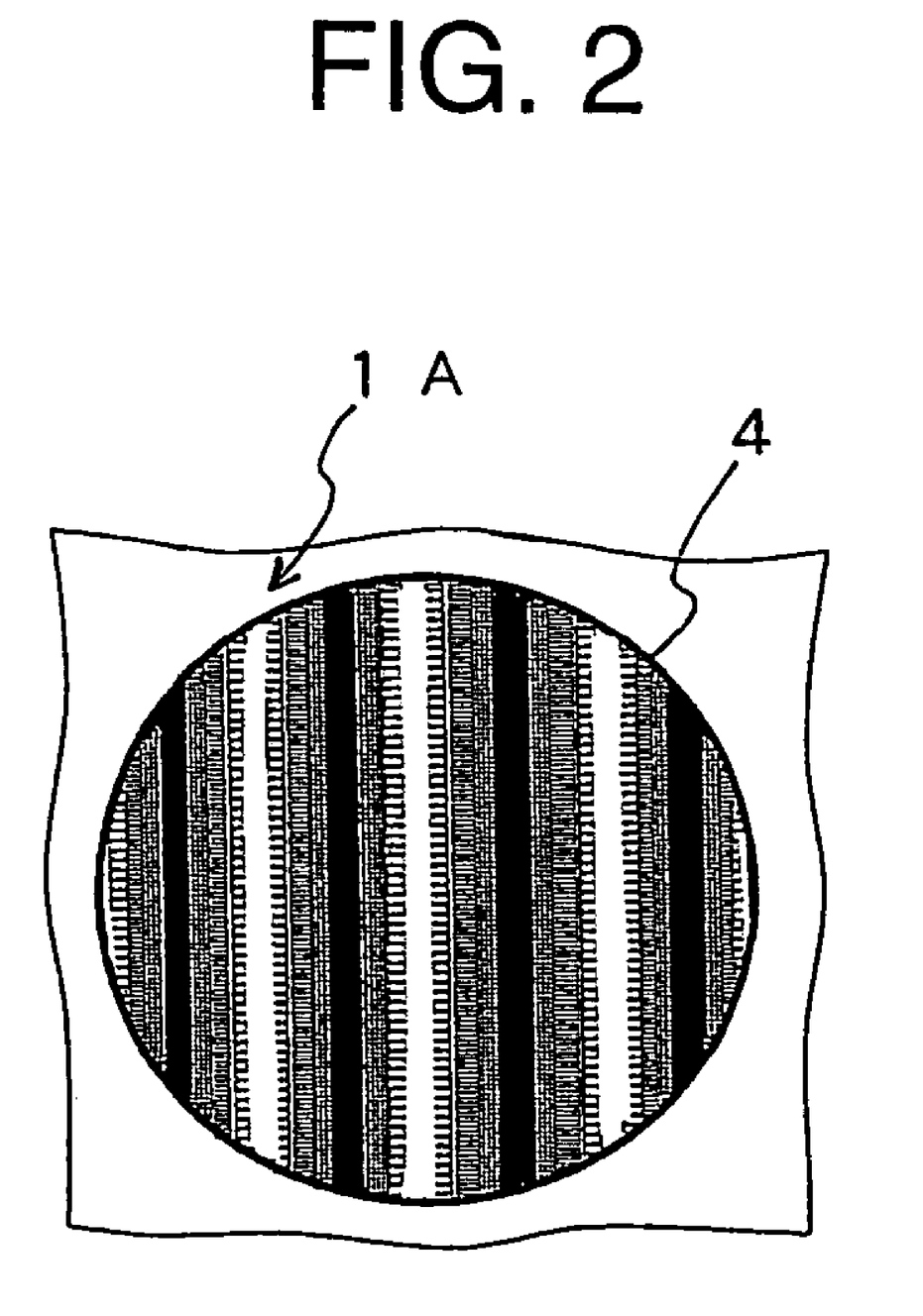
FIG. 2 is a partially enlarged front view showing the eye test chart of FIG. 1.

FIGS. 1 and 2 show the first feature of the present invention. An eye test chart 1 that assumes the form of a test plate 11 is printed in an image area 10 of about A3-size board made of synthetic resin, showing a test chart 1A on the background of bright color such as yellow.

The test chart 1A is made up of grid targets 3 composed of a grid 32 of squares arranged in a black grid pattern 31 in both the longitudinal and transverse directions, and circular targets 4 arranged inside the squares of the grid and colored with a vertically striped pattern of various color tones. Then a central square 310 is surrounded by a box frame bolder than any other squares on the grid pattern, and a circular target displayed inside the central square is set as a fixed target 40 used to fixate subjects' gaze at one specific location. The fixed target 40 may be colored with a striking hue, such as red, different from those of the other circular targets 4.

The circular target 4 shown in an enlarged view of FIG. 2, for example, has a pattern of vertical stripes colored with different hues, shades of gray, etc., or a pattern of vertical stripes of two colors that may be yellow, the same color as the background, and a color (for example, blue) different in hue from the background color. Further, each circular target 4 may be varied in color or tin, and the pattern of vertical stripes may be made with such a two-color gradation that one color shifts to the other in a sinusoidal fashion.

Using this test chart, an examiner checks if a subject can visually identify the central circular target as the fixed target 40 when viewing it with one eye from the front. It allows the examiner to examine the presence or absence of a central visual field defect caused by a disease, such as a disease in the macular area like macular degeneration or a disease of the optic nerve like optic atrophy. The examiner can also check if the subject can visually identify all parts of the test chart 1A without any break of sense to examine the presence or absence of a visual field defect or hemianopia and, if any, the type of defect.

Simultaneously, the examiner checks if the grid pattern of the grid targets 3 look skewed to the subject, thereby enabling the examination of the presence or absence of metamorphopsia caused by a disease in the macular area. Then, the examiner checks if the subject can visually identify differences in color, presence or absence of vertical striped pattern, etc. in those differently colored circular targets 4, thereby enabling the examination of the presence or absence of a color vision defect and, if any, the type of defect.

The above test chart 1A is bilaterally symmetrical about the central circular target as the fixed target 40, so that not only can both the right and left eyes be examined in the same manner, but also the presence or absence of hemianopia can be examined. It is also vertically symmetrical, so that the vertical fields of vision can be examined under the same conditions.

The following describes the procedure of eye tests using the eye test chart 1.

First of all, a subject looks through all parts of the test chart 1 with both eyes open and reads an instruction book or leaflet on the test chart to make sure the placement of respective targets, conditions, etc. Then the subject covers one eye with a special-purpose eye patch or hand from an appropriate distance from the image area 10, for example, at a position about 40 cm away from the test chart 1, and fixes his or her eye to be tested on the central fixed target 40 from the front in the vertical direction. Then the subject checks if the central square 310 and the circular target inside the central square are correctly visible.

Next, the subject checks if part or all of the grid targets 3 look skewed, dim, or missing, and if part or all of the circular targets 4 look missing or disappear from his or her eye, etc. The subject also checks if he or she can visually identify the correct colors and pattern of vertical stripes in the circular targets 4 and if there are no missing parts. These tests allow the examination of the presence or absence of symptoms of central and paracentral visual field defects, hemianopia, metamorphopsia, and color defective vision, such as congenital red-green color deficiency or acquired blue-yellow color deficiencies caused by optic nerve disorders.

During the tests, the subject should be careful not to always look away from the central fixed target 40 so that the examination will be carried out from the correct position. If an examiner witnesses the tests, he or she should keep on alerting the subject to the position of the subject's eye.

Figure 3:
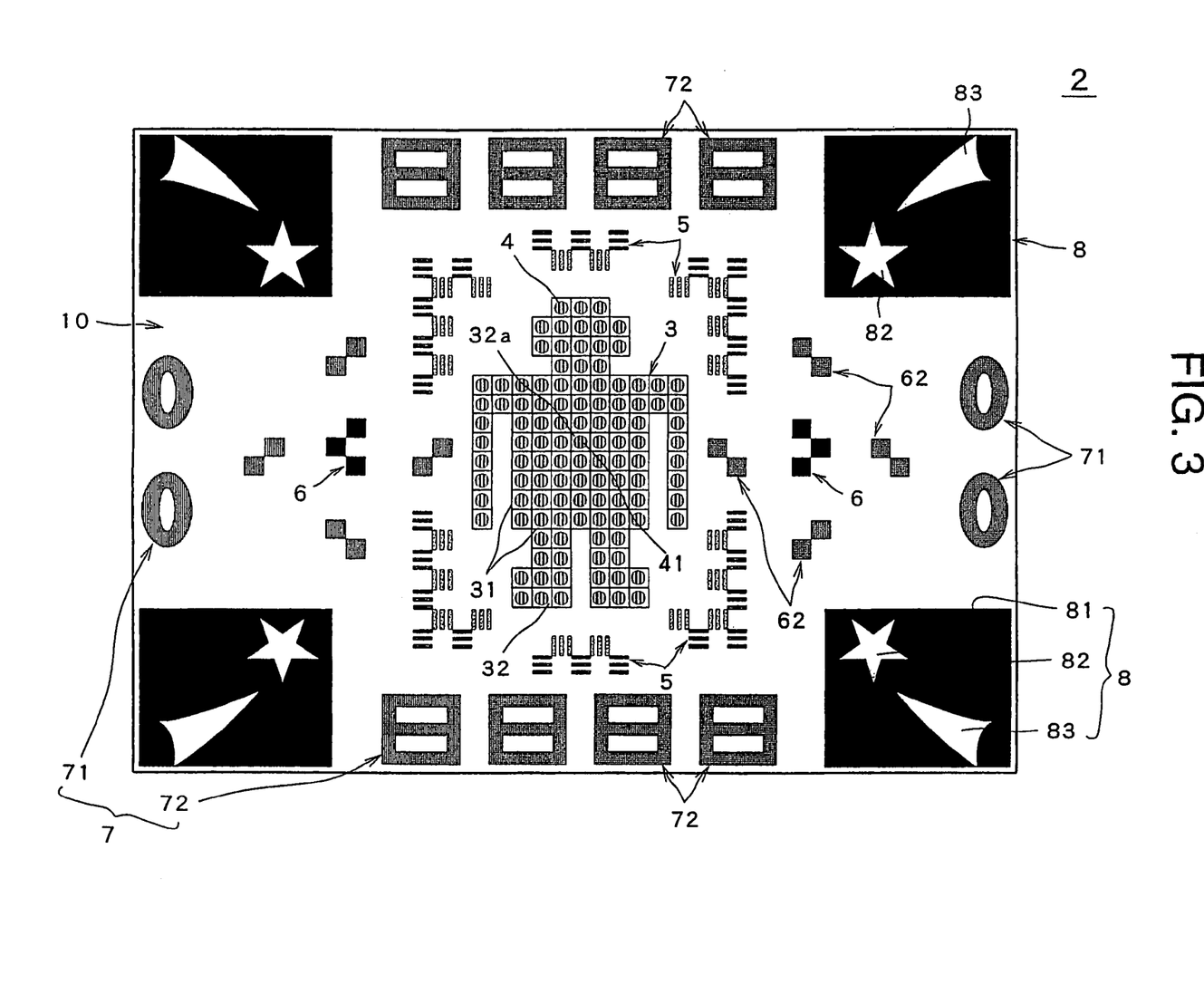
FIG. 3 is a front view showing another preferred eye test chart according to the present invention.

FIG. 3 shows the second feature of the present invention, illustrating an eye test chart 2. On the eye test chart 2, the grid pattern 31 of the grid targets 3, which is made up of the grid of squares on the eye test chart 1 in FIG. 1, is formed in the shape of a human-like robot with targets of various colors and shapes arranged around the grid pattern.

The shape, colors, pattern, etc. of the circular targets 4 in respective squares of the grid 32 are set in the same manner as those in FIG. 1, but a circular target 4 inside a central square 32a is colored with a striking hue, such as red, so that it will be set as a fixed target 41. The other circular targets 4 have a pattern of vertical stripes colored with different hues, such as yellow, the same color as the background, and another color, like blue, different in hue from the background. In this case, the tests on the presence or absence of central and peripheral visual defects, hemianopia, etc. and the tests on the presence or absence of symptoms of metamorphopsia and color defective vision can be carried out in the same manner as those using the eye test chart 1 in FIG. 1.

Further, band-shaped targets 5 composed of blocks of multiple striped patterns arranged in the shape of a band with two rows of checkered patterns are displayed around the grid targets 3. These band-shaped targets are used to detect visual impairment in the Bjerrum area. The striped pattern in each square forming part of the band-shaped targets 5 may be displayed with two different color tones that are equal in hue but contrastive in terms of the lightness of color, for example, such that the inner row is made with a vertically striped pattern of a pale color and the outer row is made with a horizontally striped pattern of a deep color. Both striped patterns may be made with a gradation in the same manner as the vertically striped pattern of the circular targets 4.

Furthermore, parallel targets 7 and large-sized square targets 8, both being larger than any other targets in the central portion, are displayed near the periphery of the image area 10. The parallel targets 7 are made up of parallel circular targets 71, each of which contains multiple 0-shaped, hollow oval figures and which are arranged at both right and left sides of the image area relative to the fixed target 41 as the center, and parallel square targets 72, each of which contains multiple figures shaped like a Chinese character "日" and which are arranged at both top and bottom sides. The multiple parallel targets of each type are displayed in parallel with each other. These targets are colored, for example, with a color that is easy to visually identify, like red or blue, against the background of yellow, but they may be displayed with any other different hue depending on the placement and shape of the parallel targets 7. On the other hand, the large-sized square targets 8, each of which contains FIGS. 82 and 83 of a falling star cut out from a large-sized black square 81 (the background color such as yellow shows through the cutouts) are displayed on the four corners of the image area 10.

The parallel targets 7 and the large-sized square targets 8 are used to examine vision in the peripheral visual field, where the retina's sensitivity is low, and mainly to examine the eye's resolution as to whether the two figures spaced at a certain distance look connected together or whether the hollow parts look filled up. These targets may be varied in size, shape, and color, and arranged at several positions around the periphery of the chart, so that a detailed examination can be made for each subject, such as the detection of a visual field defect or hemianopia, and further the detection of a nasal step in glaucoma.

Blind-spot targets formed by a combination of multiple black squares are displayed at appropriate positions bilaterally symmetrical about the fixed target 41. The blind-spot targets 6 are arranged as Mariotte's blind spot that disappears from the subject's eye gazing at the fixed target 41 from the front when the distance between the image area 10 and the eye becomes 40 cm, for example. The position of the eye at the time the blind-spot targets disappeared is decided as the position at which the eye tests are carried out. The blind-spot targets 6 are colored with a color different from those of the other targets to enable accurate determination of whether the subject can visually identify them or not, and in general, the color is black so that any subject can use them regardless of the presence or absence of color defective vision. It should be noted that the shape is not limited to the checkered pattern as shown in FIG. 3.

Then, multiple blind-spot peripheral targets 62, each of which is, for example, formed of two squares, are displayed around the blind-spot targets 6, up and down, and right and left, at an appropriate interval from the blind-spot targets 6. These targets are used to examine whether the extent of Mariotte's blind spot is widened due to a disease of the optic nerve or the optic disc such as choked disc.

The above-mentioned targets are arranged at positions bilaterally symmetrical about the fixed target 41, so that not only can both the right and left eyes be examined in the same manner, but also the presence or absence of hemianopia can be examined. They are also substantially vertically symmetrical, so that the vertical fields of vision can be examined under the same conditions in the same manner as those using the eye test chart 1 of FIG. 1.

It is preferable that all the above-mentioned targets be displayed with the color complementary to that of the background or deep colors of different hues to make it easy to distinguish from the yellow background of the image area 10. It is also preferable that they be displayed with different hues according to the position and shape of each target to make it easy to judge whether the subject can visually identify the target.

The following describes the procedure of eye tests using the eye test chart 2.

First of all, a subject looks through all parts of the test chart 2 to make sure the shape and placement of each target. Then, for pre-examination, the subject covers one eye with a special-purpose eye patch or hand from an appropriate distance from the image area 10, for example, at a position about 40 cm away from the test chart 2, and fixes his or her eye to be tested on the fixed target 41 from the front in the vertical direction to check if the large-sized square targets 8 displayed on the four corners are visible in the same way without turning his or her eye.

Then the subject checks if the vertically striped pattern of the fixed target 41 disappears from his or her eye, if part or all of the vertical stripes 31 of the grid targets 3 look skewed, dim, or missing, if the head and limb parts of the grid targets 3 arranged in the shape of a robot are visible without any missing parts, if there are missing parts in the circular targets 4 and their vertical stripes, etc. These tests are also carried out for examining the presence or absence of central visual field defects or metamorphopsia mainly caused by a disease in the macular area or the like, and the presence or absence of color defective vision caused by a disease of the optic nerve.

Next, the subject detects a position at which the blind-spot targets 6 disappear from his or her eye gazing at the fixed target 41. The blind-spot targets 6 are so arranged that they will disappear at a distance of 40 cm from the image area 10. Although subsequent eye tests are carried out at the position, when the blind spot targets 6 do not disappear even if the subject changes the distance between the image area 10 and the eye around 40 cm little by little, the distance of 40 cm is maintained throughout the remaining eye tests by measuring it with a ruler.

Then, when the blind-spot targets 6 has disappeared, the subject checks if all parts of the blind-spot peripheral targets 62 arranged around the blind-spot targets 6 are visible from the position to examine whether Mariotte's blind spot is widened or not.

Then, the subject checks if the checkered pattern of the band-shaped targets 5 arranged around the grid targets 3 are correctly visible as the checkered pattern, if the color of the squares in the same row looks different, and if the striped pattern looks correctly.

After that, tests on the peripheral visual field are carried out using each target arranged around the periphery of the image area 10. First of all, the subject checks if the star 82 and the band 83 in the large-sized square targets 8 displayed on the four corners with the shape of the falling star cut out from the black squares are seen as separate from each other, if the large-sized targets 8 on the four corners look the same, and if the black squares 81 look skewed, and then checks if each set of the parallel targets 7, composed of the parallel square targets 72 shaped like a Chinese character "日" and arranged in parallel at both top and bottom sides, and the 0-shaped parallel circular targets 71 arranged in parallel at both right and left sides, looks like the same figures are in line with each other, and if no parts look missing or skewed.

During the tests, the subject should be careful not to always look away from the fixed target 41 so that the examination will be carried out from the correct position. If an examiner witnesses the tests, he or she should keep on alerting the subject to the position of the subject's eye.

Figure 4:
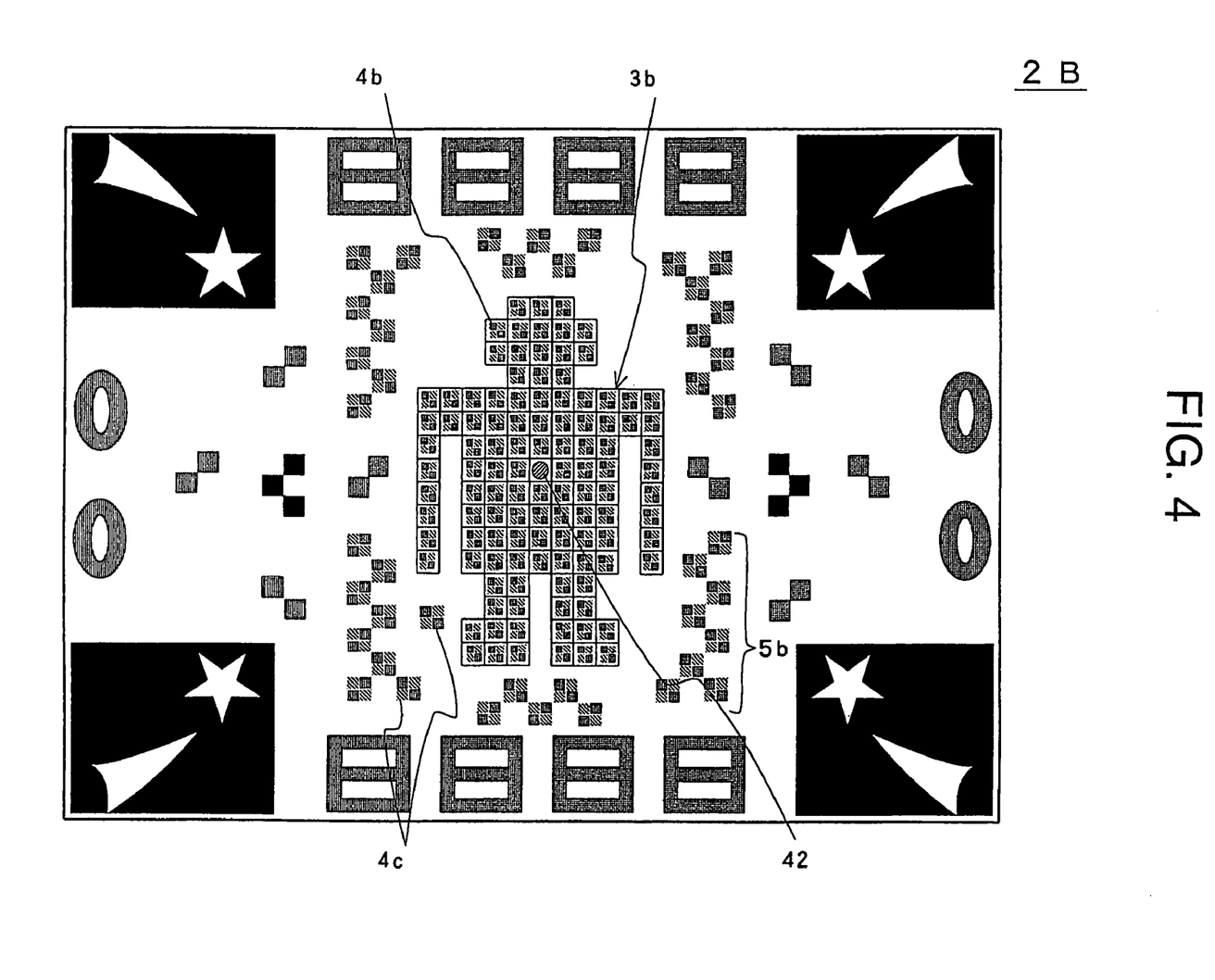
FIG. 4 is a front view showing still another preferred eye test chart according to the present invention.

FIG. 4 shows the third feature of the present invention, illustrating an eye test chart 2B. The eye test chart 2B is such that grid targets 3b are used instead of the circular targets 4 arranged inside the grid targets 3 on the eye test chart of FIG. 3. The grid targets 3b contains square targets 4b, each of which is divided into four squares in a checkered pattern of a combination of two kinds of colors different in hue, for example. Further, instead of the band-shaped targets 5 arranged around the grid targets 3 in the shape of the band with the checkered patterns of the multiple stripes, large-sized square targets 4c enlarged from the square targets 4b are used as elements of band-shaped targets 5b arranged in the shape of a band of checkered patterns around the grid targets 3b. This chart particularly allows for the detection of a glaucomatous visual field defect and a scotoma created by macular degeneration.

It should be noted that a fixed target 42 on the eye test chart 2B is a circular target colored with a striking color like red and arranged in one of the grid targets 3b located at the center of the robot.

Each of the square targets 4b is made up of four divided squares in a checkered pattern (patch pattern) of two kinds of colors different in hue from yellow as the background color. The two kinds of colors are different in hue, for example, to enable a normal eye to determine the checkered pattern. Even when the two kinds of colors have the same lightness, they can be easily distinguished if they are complementary colors, like orange and green. The square targets 4b enable even subjects of low visual sensitivity to identify the difference of colors compared to the circular targets 4 with the striped pattern forming each circle.

The band-shaped targets 5b composed of the enlarged square targets 4c and arranged around the grid targets 3b are made up of elements formed by enlarging the square targets 4b, and they are easier to identify than the striped patterns of the band-shaped targets 5 of FIG. 3. The other targets on the eye test chart 2B are the same as those on the eye test chart 2 of FIG. 3, and the procedure and method are also the same.

The detection percentage of glaucomatous visual field defects is 50 percent or more at Stage I, 80 to 90 percent at Stage II and Stage III, 100 percent at Stage IV and Stage V in the Classification of Glaucomatous Progression by the Auhlhorn-Greve modified method using Humphrey perimeter. Some other glaucoma screening techniques have been reported so far, but none of them shows a higher rate of detection than that achieved using this chart even at Stage I and Stage II.

Figure 5:
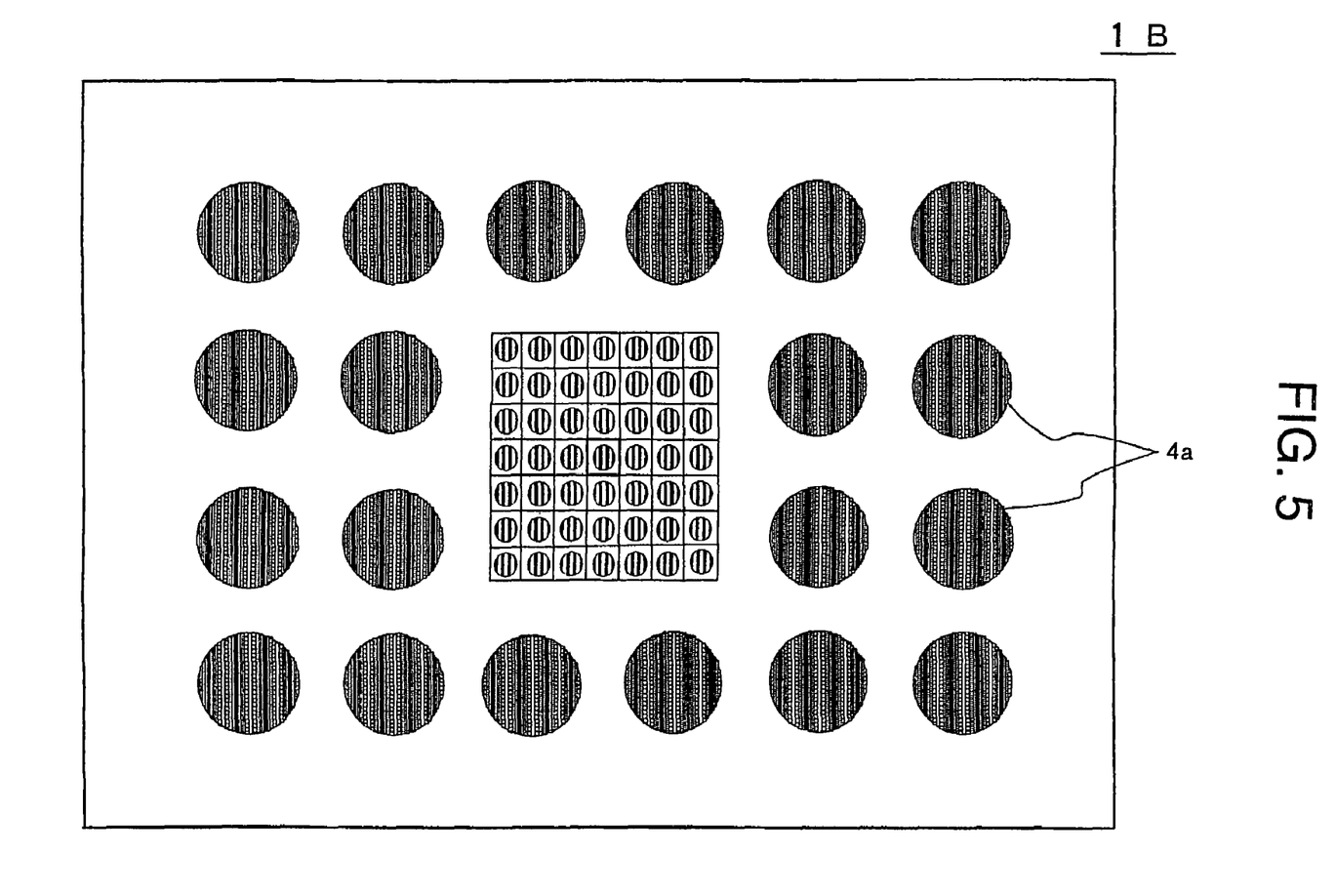
FIG. 5 is a front view showing yet another preferred eye test chart according to the present invention.

FIG. 5 shows the fourth feature of the present invention, illustrating an eye test chart 1B on which enlarged circular targets 4a enlarged from the pattern of the circular targets 4 arranged inside the grid targets 3 are arranged vertically and horizontally in parallel. The enlarged circular targets 4a enable even a subject with too low visual acuity to identify the circular targets in the grid targets 3 or a subject with low sensitivity in the peripheral visual field to undergo the tests. The test procedure and method using this chart are the same as those using the eye test chart 1 of FIG. 1 except for the enlarged circular targets 4a.

Figure 6:
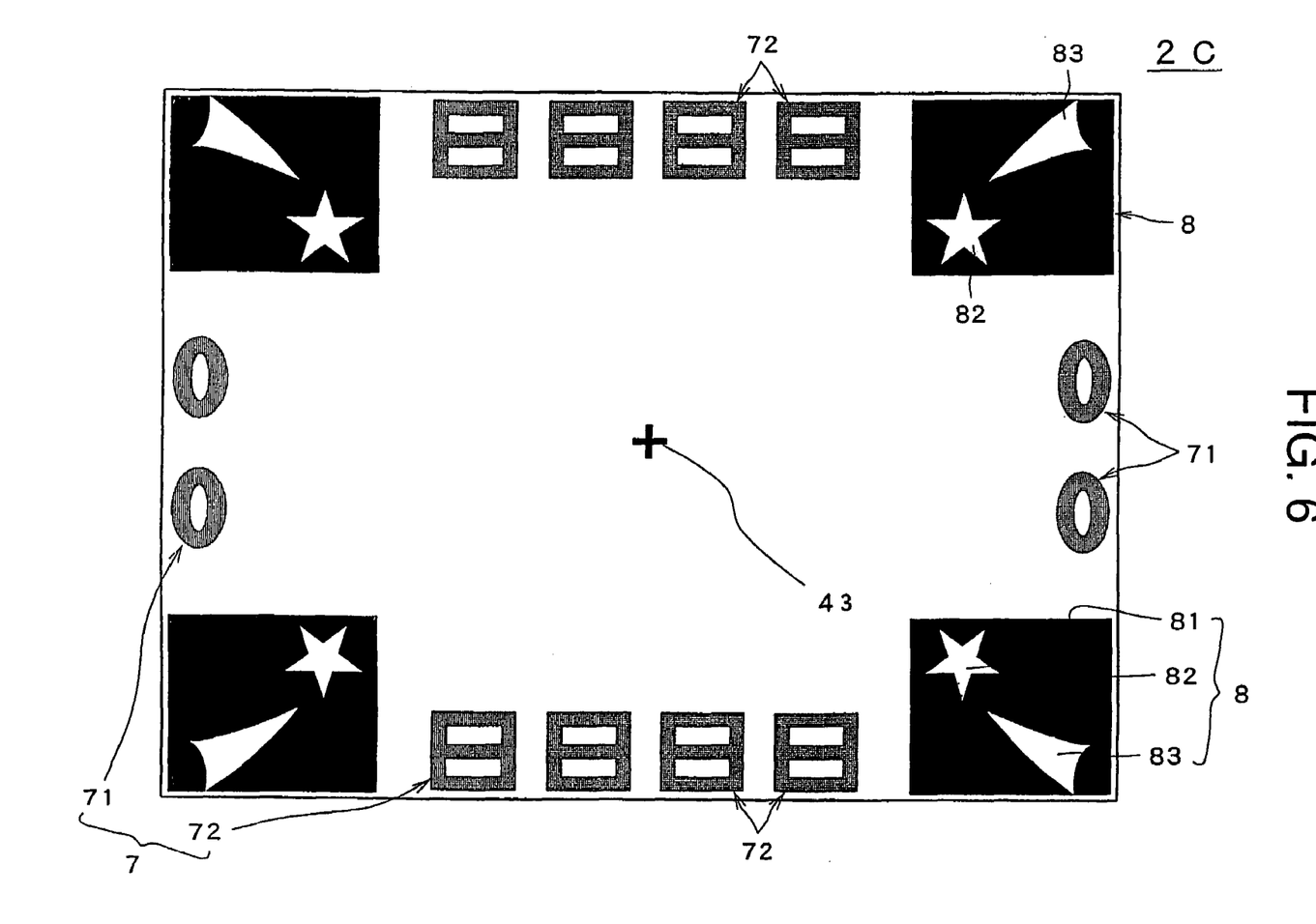
FIG. 6 is a front view showing yet another preferred eye test chart according to the present invention.

FIG. 6 shows the fifth feature of the present invention, illustrating an eye test chart 2C. Arranged on the eye test chart 2C are targets extracted from the eye test chart in FIGS. 3 and 4 mainly for the purpose of examining the eye's resolution. This chart aims to make it easy to carry out the tests on cases of persons who have a reduced ability to judge. A fixed target 43 of an easy-to-perceive shape, such as a black cross, is arranged at the center of the chart. This chart is vertically and laterally symmetrical, so that not only the eye's resolution but also visual differences between both eyes or hemianopia can be examined.

Figure 7:
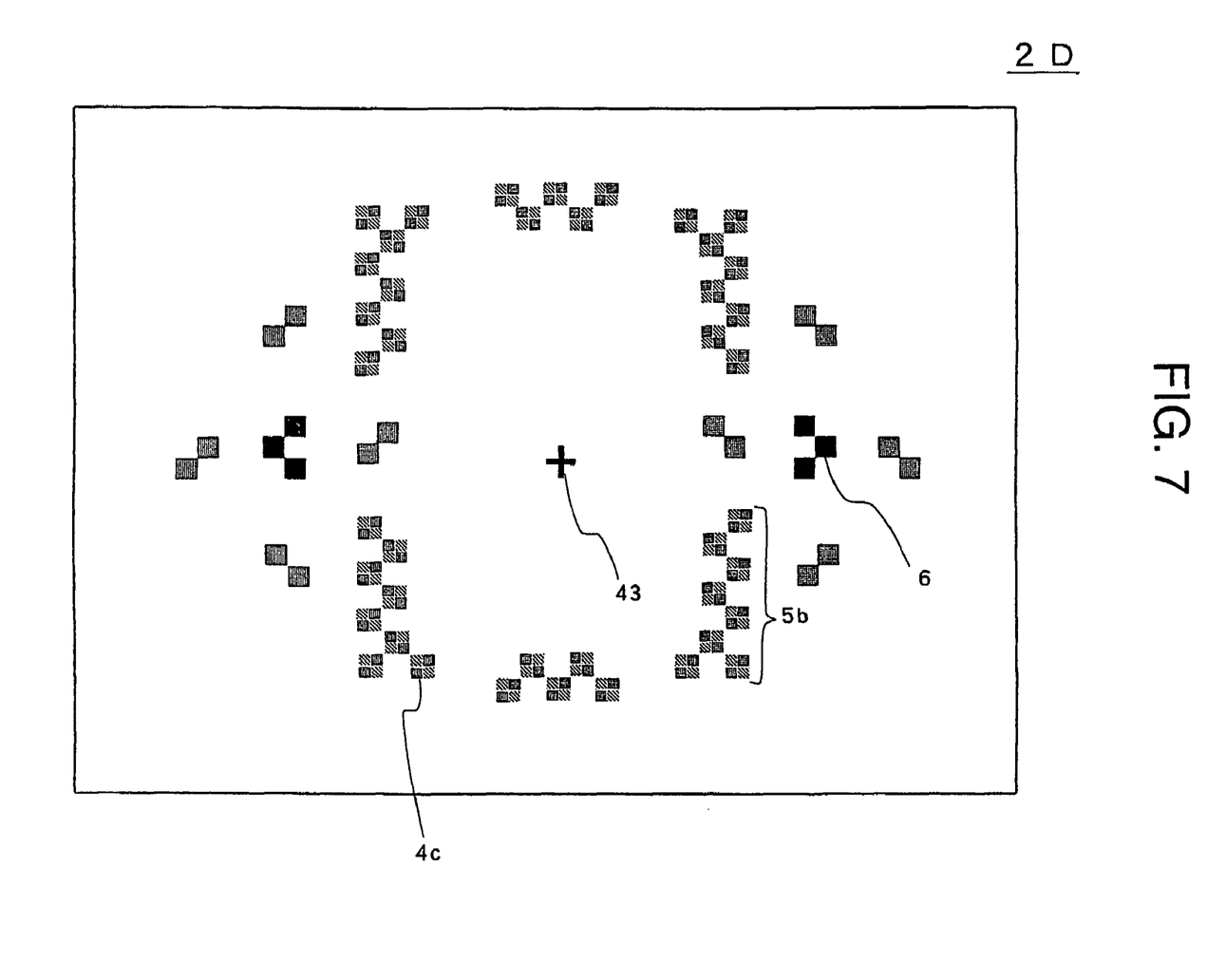
FIG. 7 is a front view showing the other preferred eye test chart according to the present invention.

FIG. 7 shows the sixth feature of the present invention, illustrating an eye test chart 2D on which the band-shaped targets 5b, the Mariotte's blind-spot targets 6, and the blind-spot peripheral targets 62 extracted from the eye test chart 2B in FIG. 4 are arranged. Like in FIG. 6, this chart aims to make it easy to carry out the tests on cases of persons who have a reduced ability to judge. Also, like in FIG. 6, the black-cross fixed target 43 is placed at the center. The use of this chart enables a subject with too low visual acuity to identify the checkered pattern of each of the square targets 4b inside the grid targets 3b on the eye test chart 2B, or a subject who has a reduced ability to judge, to visually identify the band-shaped targets 5b composed of the enlarged square targets 4c on the visually simplified, easy-to-view eye test chart 2D, while maintaining the correct distance between the eye test chart and the eye.

Although the above discloses the best modes for carrying out the present invention, the shape and placement of each target are not limited to those shown in each figure, and the targets may have any color tone and shape, as long as they are clearly contrastive or distinct, within the technical scope of the present invention.

The eye test scheme according to the present invention is such that multiple targets displayed for the purpose of examining different symptoms respectively in the manner mentioned above are arranged on one chart, thereby allowing eye tests of multiple items to be carried out at the same time. This reduces test time and fatigue of the subject, and hence makes it easy to conduct the eye tests on subjects of all levels of condition. Further, since multiple targets of different colors and shapes defined according to their positions are arranged on the chart, it is clear whether the subject can visually identify them or not. Furthermore, since the subject undergoes the examination after checking the placement and shape of each target, he or she can recognize any abnormal region in his or her body and becomes aware of it. Furthermore, the examiner does not need expert knowledge and skills, so that detailed tests can easily be conducted not only at the Department of Ophthalmology or eye clinic but also at any other Department or places other than medical institutions. In addition, the eye test charts can be manufactured at low cost by printing them on synthetic resin plates, paper, etc., so that they can be placed in the waiting room at a medical institution or pharmacy, or distributed to ordinary offices, houses, etc. It can be helpful for subjects to make a self-diagnosis and early detection of visual field defects and the like. Furthermore, since the eye test charts are small and light in weight, any person or examiner may hold a test chart up to adjust the position so that a subject can undergo the examination without changing his or her position. It enables even a bedridden patient with a brain disease or the like to undergo the examination.

INDUSTRIAL APPLICABILITY

As described above, the eye test chart scheme according to the present invention is such that multiple targets of various colors and shapes displayed for the purpose of examining different symptoms respectively are arranged on one chart, thereby allowing eye tests of multiple items to be carried out at the same time. Since it reduces test time and fatigue of the subject, it is useful for the eye tests.

Further, the targets have different colors and shapes, and this makes it easy to judge whether the subject can visually identify the targets or not. Thus, since the subject can become area of abnormal regions in his or her body, it is suitable for self-diagnosis of color defective vision.

Further, the examiner does not need expert knowledge and skills, and it is useful for eye tests not only at the Department of Ophthalmology or eye clinic, but also at any other Department or places other than medical institutions.

Furthermore, the eye test charts can be manufactured at low cost, so that they can be carried around or placed at various locations. Since this makes it easy for anyone to undergo the examination, the eye test charts are suitable for early detection and progress observation of an eye or brain disease that causes a visual defect. In addition, since the eye test charts are light in weight and conveniently portable, they are also suitable for medical checks or house visits by doctors on request.

The invention claimed is:

1. An eye test chart apparatus comprising visual targets for multiple test purposes and a fixed target centrally positioned relative to the positions of said visual targets, wherein said visual targets are composed of patterns of combinations of at least two or more kinds of colors and predetermined shapes, and are arranged at predetermined positions on an image area corresponding to visual field regions to be examined, and wherein said fixed target is visually distinguishable from said visual targets, whereby color vision defects and their abnormal regions can be identified as a result of subject's visual identification of the visual targets arranged at the predetermined positions.

2. An eye test chart apparatus according to claim 1, wherein said visual targets comprise circular or square targets.

3. An eye test chart apparatus according to claim 2, wherein said at least two or more kinds of colors are two kinds of colors different in hue from each other.

4. An eye test chart apparatus according to claim 3, wherein said at least two or more kinds of colors are complementary colors.

5. An eye test chart apparatus according to claim 1, 2, 3, or 4, wherein said visual targets comprise circular or square targets divided into four parts in a checkered pattern of a combination of two kinds of colors different from the background color.

6. An eye test chart apparatus according to claim 1, 2, 3, or 4, wherein said visual targets comprise circular or square targets each composed of a vertical striped pattern of two different kinds of colors.

7. An eye test chart apparatus according to claim 6, wherein said vertical striped pattern is formed such that one color shifts to the other in a sinusoidal fashion.

8. An eye test chart apparatus according to claim 1, 2, 3, or 4, wherein said fixed target has a color or colors different from those of said visual targets, or a profile line bolder than those of said visual targets, and wherein said visual targets comprise grid targets composed of a grid of squares in which circular or square targets are arranged in parallel around said fixed target in both the longitudinal and transverse directions.

9. An eye test chart apparatus according to claim 8, wherein said visual targets further comprise enlarged circular or square targets arranged in parallel around said grid targets in both the longitudinal and transverse directions, and wherein said enlarged circular or square targets are formed by enlarging the pattern of said circular or square targets arranged inside said grid targets.

10. An eye test chart apparatus according to claim 1, 2, 3, or 4, wherein said visual targets comprise band-shaped targets formed in the shape of a band with a checkered pattern of multiple squares, each composed of a striped pattern or checkered pattern with four divided parts, and wherein said band-shaped targets are arranged around said fixed target vertically and horizontally in parallel.

11. An eye test chart apparatus according to claim 1, 2, 3, or 4, wherein said visual targets comprise a set of blind-spot targets for determining Mariotte's blind spot, composed of a combination of one or more black figures, and arranged at a predetermined position on said eye test chart in a bilaterally symmetrical pattern.

12. An eye test chart apparatus according to claim 11, wherein said visual targets comprise blind-spot peripheral targets, composed of multiple figures colored with a color different from the background color and easy to visually identify on the background color, and arranged around said blind-spot targets in a bilaterally symmetrical pattern.

13. An eye test chart apparatus according to claim 1, 2, 3, or 4, wherein said visual targets comprise large-sized square targets, each of which is a black square larger than any other single circular or square target, and which contains two figures colored with the background color or a color of high lightness and spaced at a predetermined interval, and wherein said large-sized square targets are arranged on four corners of said eye test chart.

14. An eye test chart apparatus according to claim 1, 2, 3, or 4, wherein said visual targets comprise at least two or more parallel square targets, each of which is composed of a hollow figure shaped like a Chinese character "日" with the figure parts colored with a color different from the background color and easy to visually identify on the background color and the hollow parts colored with the background color, and wherein said parallel square targets are arranged at both top and bottom sides, or at both right and left sides, in parallel in the transverse or longitudinal direction.

15. An eye test chart apparatus according to claim 1, 2, 3, or 4, wherein said visual targets comprise at least two or more parallel circular targets, each of which is composed of a hollow figure shaped like a number "0" with the figure parts colored with a color different from the background color and easy to visually identify on the background color and the hollow parts colored with the background color, and wherein said parallel circular targets are arranged at both top and bottom sides, or at both right and left sides, in parallel in the transverse or longitudinal direction.

16. An eye test chart apparatus according to claim 1, 2, 3, or 4, wherein said visual targets are arranged in a bilaterally symmetrical pattern.

* * * * *